United States Patent
Heide et al.

(10) Patent No.: US 11,344,660 B2
(45) Date of Patent: May 31, 2022

(54) DEVICE COMPRISING A MULTI-LUMEN TUBE AND ITS USE

(71) Applicant: FRESENIUS MEDICAL CARE DEUTSCHLAND GMBH, Bad Homburg (DE)

(72) Inventors: Alexander Heide, Eppstein (DE); Arne Peters, Bad Homburg (DE); Martin Weitz, Bad Homburg (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 87 days.

(21) Appl. No.: 15/510,325

(22) PCT Filed: Sep. 9, 2015

(86) PCT No.: PCT/EP2015/001819
§ 371 (c)(1),
(2) Date: Mar. 10, 2017

(87) PCT Pub. No.: WO2016/037702
PCT Pub. Date: Mar. 17, 2016

(65) Prior Publication Data
US 2017/0296737 A1    Oct. 19, 2017

(30) Foreign Application Priority Data
Sep. 10, 2014    (DE) ..................... 10 2014 013 419.9

(51) Int. Cl.
*A61M 1/36*    (2006.01)
*F28D 7/00*    (2006.01)
(Continued)

(52) U.S. Cl.
CPC ........ *A61M 1/3661* (2014.02); *A61M 1/1664* (2014.02); *A61M 1/3621* (2013.01);
(Continued)

(58) Field of Classification Search
CPC combination set(s) only.
See application file for complete search history.

(56) References Cited

U.S. PATENT DOCUMENTS

| 5,403,281 A | 4/1995 | O'Neill et al. |
| 5,814,016 A | 9/1998 | Valley et al. |
(Continued)

FOREIGN PATENT DOCUMENTS

| DE | 202007015930 | 3/2008 | |
| DE | 112012001381 | 1/2014 | |
| WO | WO2016037702 A1 * | 3/2016 | ............. A61M 1/36 |

OTHER PUBLICATIONS

Machine Translation of WO 2016/037702 A1, pp. 1-15 (Year: 2016).*

*Primary Examiner* — Hayden Brewster
(74) *Attorney, Agent, or Firm* — Jacobson Holman PLLC

(57) ABSTRACT

The present invention relates to an apparatus comprising at least one multi-lumen tube, wherein the tube has a first group of lumens and a second group of lumens wherein the lumens of the second group are arranged around the lumen(s) of the first group, and wherein the lumen(s) of the first group serve the transportation of at least one first fluid, and wherein the lumens of the second group are filled with at least one functional fluid, wherein the apparatus furthermore comprises at least one actuator which is in communication with at least one of the second lumens and is configured such that at least one property of the functional fluid can be changed by means of the actuator.

14 Claims, 2 Drawing Sheets

(51) Int. Cl.
  *A61M 1/16* (2006.01)
  *F28F 1/02* (2006.01)
  *F28D 21/00* (2006.01)

(52) U.S. Cl.
  CPC ............ *F28D 7/0008* (2013.01); *F28F 1/022* (2013.01); *A61M 2205/3331* (2013.01); *A61M 2205/3334* (2013.01); *A61M 2205/3368* (2013.01); *A61M 2205/366* (2013.01); *A61M 2205/3633* (2013.01); *F28D 2021/005* (2013.01)

(56) References Cited

U.S. PATENT DOCUMENTS

| | | | | |
|---|---|---|---|---|
| 6,818,012 | B2* | 11/2004 | Ellingboe | A61F 7/0085 607/104 |
| 9,907,897 | B2* | 3/2018 | Burbank | A61M 1/1672 |
| 2002/0156451 | A1* | 10/2002 | Lenker | A61M 5/44 604/500 |
| 2003/0093027 | A1 | 5/2003 | McGuckin, Jr. et al. | |
| 2006/0212026 | A1* | 9/2006 | Abboud | A61B 18/02 606/20 |
| 2007/0181499 | A1* | 8/2007 | Roberts | A61M 1/3472 210/645 |
| 2008/0200906 | A1* | 8/2008 | Sanders | A61M 1/0001 604/543 |
| 2009/0312727 | A1* | 12/2009 | Heaton | A61M 27/00 604/318 |
| 2010/0006263 | A1* | 1/2010 | Johnson | A61M 5/44 165/104.19 |
| 2011/0105846 | A1* | 5/2011 | Yoshie | A61B 1/12 600/158 |
| 2011/0227237 | A1 | 9/2011 | Hertz | |
| 2013/0237903 | A1* | 9/2013 | Klewinghaus | A61M 39/24 604/28 |
| 2019/0046785 | A1* | 2/2019 | Weaver | A61M 1/3661 |

* cited by examiner

DEVICE COMPRISING A MULTI-LUMEN TUBE AND ITS USE

The present invention relates to an apparatus having at least one multi-lumen tube.

The use of multi-lumen tubes is known, for example, from the area of catheter technology.

As part of extracorporeal blood treatment, such as in dialysis, one major aspect is that a kinking of the tubes used has to be prevented in order not to put the patient and the success of the treatment at risk. To date, a check of the tubes with respect to kinking took place by a visual check by the user or by the determination of unusual treatment parameters such as unusual pressure values.

On the use of acute dialysis machines for therapy processes using plasma replacement, the blood returned to the patient has to be heated to protect the patient from becoming hypothermic. This is typically done in acute dialysis indirectly via the heating of the dialyzate fluid or substitute fluid. Since, however, neither a substitute nor a dialyzate are used in therapeutic processes using plasma replacement, the tubing sets do not comprise the apparatus (heating bags) typical in acute dialysis for the heating of these fluids. An external heating device therefore has to be used which has to additionally be installed at the acute dialysis machine and into which parts of the tubing set have to be placed to heat them.

Figure 1:
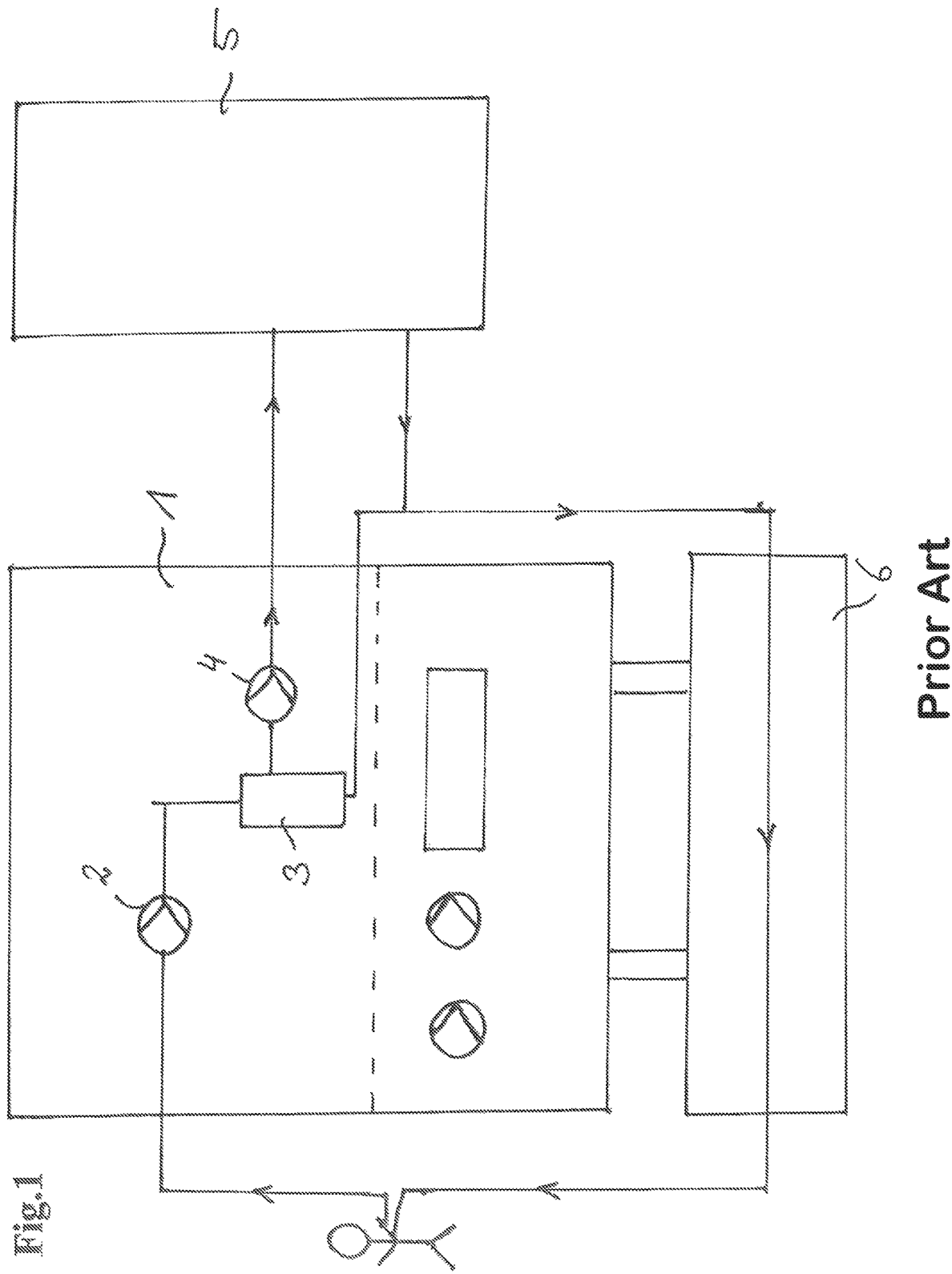

The setup for a therapeutic process using plasma replacement is shown in FIG. 1. The blood is pumped to the dialyzer 3 via the blood pump 2 of the acute dialysis machine 1. The plasma filtered by means of the filtration pump 4 enters into the device 5 for purification and is subsequently fed back into the blood return line to the patient. The return line is conducted through the external heating element 6 to heat the purified blood to the desired temperature.

This additional heating device degrades the drain flow behavior of the therapeutic system and has to be operated separately. The additional heating device furthermore increases the cleaning and disinfection effort and disadvantageously influences the outer appearance and the total weight and thus the position of center of gravity of the acute dialysis machine 1.

It is the underlying object of the present invention to further develop an apparatus of the initially named kind such that it allows a target-oriented use of the tube and in particular makes possible the prevention of a kink state of the tube.

This object is achieved by an apparatus of the present invention having the features described below.

Provision is accordingly made that the multi-lumen tube has a first group of lumens and a second group of lumens, wherein the lumen(s) of the second group is/are arranged around the lumen(s) of the first group, wherein the lumen(s) of the first group serve(s) the transportation of a fluid, and wherein the lumens of the second group are filled with at least one functional fluid. Provision is furthermore made that the apparatus comprises at least one actuator which is in communication with at least one of the second lumens and which is configured such that at least one property of the functional fluid can be changed by means of the actuator.

This property of the functional fluid can, for example, be its pressure. If it is found that the tube is kinked, the pressure of the functional fluid in at least one lumen of the second group can be increased, which counteracts a kinking of the tube. On or after a kinking has taken place, the kinking can thus be terminated by pressure modulation in the outer lumen(s) without the medium to be transported having to be influenced in the lumen of the first group.

The medium to be transported can, for example, be a bodily fluid and can in particular be blood or also a treatment fluid and in particular a dialysis solution.

The present invention relates to an apparatus whose at least one first lumen is filled with a fluid and to an apparatus whose at least one first lumen is empty and is to be filled with a fluid to be transported.

The procedure of preventing the kinking by pressure modulation is an exemplary possibility of the use of the apparatus in accordance with the invention, but the invention is not restricted thereto.

The lumen(s) of the first group, that is the inwardly disposed lumen(s), can be configured by the pressure action in the outer lumen(s), i.e. the lumen(s) of the second group, such that the wall thickness of said lumen(s) of the first group can be reduced since a sufficient mechanical stability is already achieved by the outwardly disposed lumens.

A material saving is thus possible since the demands on the pressure stiffness are reduced accordingly.

The phrases that "the lumen(s) of the second group is/are arranged around the lumen(s) of the first group" or is/are "outwardly disposed", "inwardly disposed" etc. are not to be understood in a restrictive manner such that the lumen(s) of the second group has/have to completely surround the lumen(s) of the first group, although this is a preferred embodiment of the invention. The case is also covered by the invention that, for example, only two lumens of the second group are provided which take up one or more lumens of the first group between them.

The change in the pressure is only one conceivable embodiment of the invention. The case is also covered by the invention that any other desired properties of the functional fluid can be influenced by the actuator. It is thus conceivable that the actuator is configured such that the volume flow and/or the temperature of the functional fluid can be changed by means of the actuator.

On a temperature control, a heating fluid can flow through the lumen or lumens of the second groups to bring the fluid transported in the lumen or lumens of the first group to a desired temperature level or to hold it thereat. It is, for example, conceivable that an integrated heating circuit can be implemented by the apparatus to control the temperature of the patient blood and/or a substituate and/or a dialyzate transported in the first group.

Furthermore, at least one sensor can be provided which is configured such that it determines at least one property of the functional fluid and/or of the transported fluid and/or of at least one lumen. It is thus conceivable that the pressure loss which is generated by the lumen(s) of the second group and which depends on the kink state is measured and that a property of the functional fluid such as its pressure is changed in dependence thereon.

It is also conceivable that the actuator is configured such that it changes the temperature of the functional fluid in dependence on the temperature of the transported fluid. It is thus also conceivable that, in addition to a passive thermal insulation by the outwardly disposed lumen(s), which can be filled with air, for example, for this purpose, an active heating or cooling takes place in that a hot or cold fluid, such as preheated air, is conducted through or is located in the outwardly disposed lumen(s).

As stated above, a conceivable embodiment of the invention comprises the actuator being configured such that it changes the pressure of the functional fluid in dependence on the flow resistance of one or more of the lumens of the second group. If it is determined that this flow resistance, i.e. the pressure loss present, exceeds a limit value, a conclusion can be drawn that a kinking of the tube is present. In this case, the actuator can increase the pressure to a predefined value or can at least increase it for so long until the flow resistance again lies in an acceptable range.

The functional fluid can, for example, be a gas such as compressed air or a liquid.

The present invention furthermore relates to the use of an apparatus in accordance with the present invention in a blood treatment device, in particular in a dialysis machine. Such a use is, for example, conceivable to the extent that at least one tube or tube section is formed by a multi-lumen tube in accordance with the invention. This tube or tube section can, for example, form a component of or the total extracorporeal circuit of a blood treatment device.

If the multi-lumen tube(s) or its or their inner lumen belonging to the first group is connected to the patient, the advantage results that the mass which the patient carries on his arm is comparatively small since this lumen can be configured as thin-walled. A further advantage for the patient comprises the increased safety since—as stated above—a kinking of the tube can be effectively remedied in an automated manner by the actuator.

There is furthermore an advantage in that the required heating power for the blood treatment device, in particular for the dialysis machine, is reduced since the outwardly disposed tubes form a thermal insulation.

The apparatus can optionally also be used for heating the blood return line to the patient. External heating circuits having external heating elements have previously been used here, in particular on the use of so-called acute dialysis machines, for example for therapeutic processes using plasma replacement. Internal pumps and heating elements of the machine can be used by the use of the multi-lumen tube.

The present invention furthermore relates to a blood treatment device, in particular to a dialysis machine, having at least one extracorporeal circuit, with the blood treatment device being configured with at least one apparatus in accordance with the present invention and with the extracorporeal circuit being formed at least sectionally by the multi-lumen tube of the apparatus.

In an advantageous embodiment, the blood return to the patient takes place via the lumen or lumens of the first group. A heating fluid flows via the lumen or lumens of the second group to heat the returned blood to the required temperature. The heating fluid can, for example, be a saline solution.

The blood to be returned does not have to be redirected via an external heating system, but can rather be conducted back to the patient on a direct path. A heating of the purified blood flow to the desired temperature level can take place in parallel. The patient is effectively protected from becoming hypothermic.

The blood treatment device ideally comprises an internal heating fluid reservoir. Alternatively or additionally, a connection of an external heating fluid reservoir is conceivable. Furthermore, an internal pump and/or an internal heating element can be provided for the conveying and/or temperature control of the heating fluid. The use of an external heating device has previously contributed to a deterioration in the drain flow behavior of the therapeutic system. In addition, external devices have to be operated separately, increase the cleaning and disinfection effort and influence the outer appearance and the total weight and thus the position of center of gravity of the blood treatment device.

The blood treatment device can, for example, be a device for acute dialysis. If such a device is used for therapeutic processes using plasma replacement, e.g. as part of a therapeutic apheresis, neither substituate nor dialysis fluid are required. The substituate pump provided in the device and the heating element are then available for the conveying and heating of the heating fluid.

In this sense, the invention likewise relates to a use of the blood treatment device for therapeutic processes using plasma replacement, in particular for therapeutic apheresis.

The present invention furthermore relates to a method of operating an apparatus in accordance with the present invention, with the method comprising the step of changing at least one property of the functional fluid. As stated above, this property can be the temperature, the pressure, the flow speed or the volume flow, etc. of the functional fluid.

The method preferably comprises the step of increasing the pressure in at least one lumen of the second group when a kinking of the tube has been determined.

The kinking of the tube can be detected, for example, in that the functional fluid is conducted through at least one lumen of the second group and in that the pressure drop of the functional fluid in the throughflow is measured.

If the pressure drop exceeds a limit value or if the pressure drop increases over time, a conclusion of a kinking can be made.

It is conceivable within the course of this procedure that at least two lumens of the second group are connected to one another, with the functional fluid flowing through a lumen of the second group in a first direction and subsequently being diverted and flowing through a further lumen of the second group in a second direction opposite to the first direction and with the pressure drop of the functional fluid in the throughflow being measured. The dialysis machine or another blood treatment device or device recognizes the loss-free throughflow. If thus a pressure increase occurs, a conclusion can be drawn that the tube is kinked.

At least one valve arrangement can be used to "short circuit", i.e. to connect, the two or more than two lumens of the second group.

To end the kinking, it is conceivable that the pressure in the lumen of the second group is increased for so long until the pressure drop falls below a specific limit value. Alternatively to this, the pressure in the lumen of the second group can be increased up to a reaching of a predefined value at which it is assumed that kinking is no longer present.

The present invention furthermore comprises the transfer of information and/or energy by a property change of the functional fluid and preferably by a pressure change or by pressure pulses of the functional fluid.

The pressure in the lumen(s) of the second group can, for example, thus be used by pressure modulation as a line medium for signals or energy.

It is conceivable that at least one valve is provided that is arranged such that it is opened or closed by the property change of the functional fluid or that this is released by a discriminant triggered by the passage of the pressure value.

It is also conceivable that the method comprises the step of measuring the temperature of the fluid flowing through the lumen(s) of the first group and, in dependence thereon, a property change such as a change of the temperature of the functional fluid.

Figure 2:
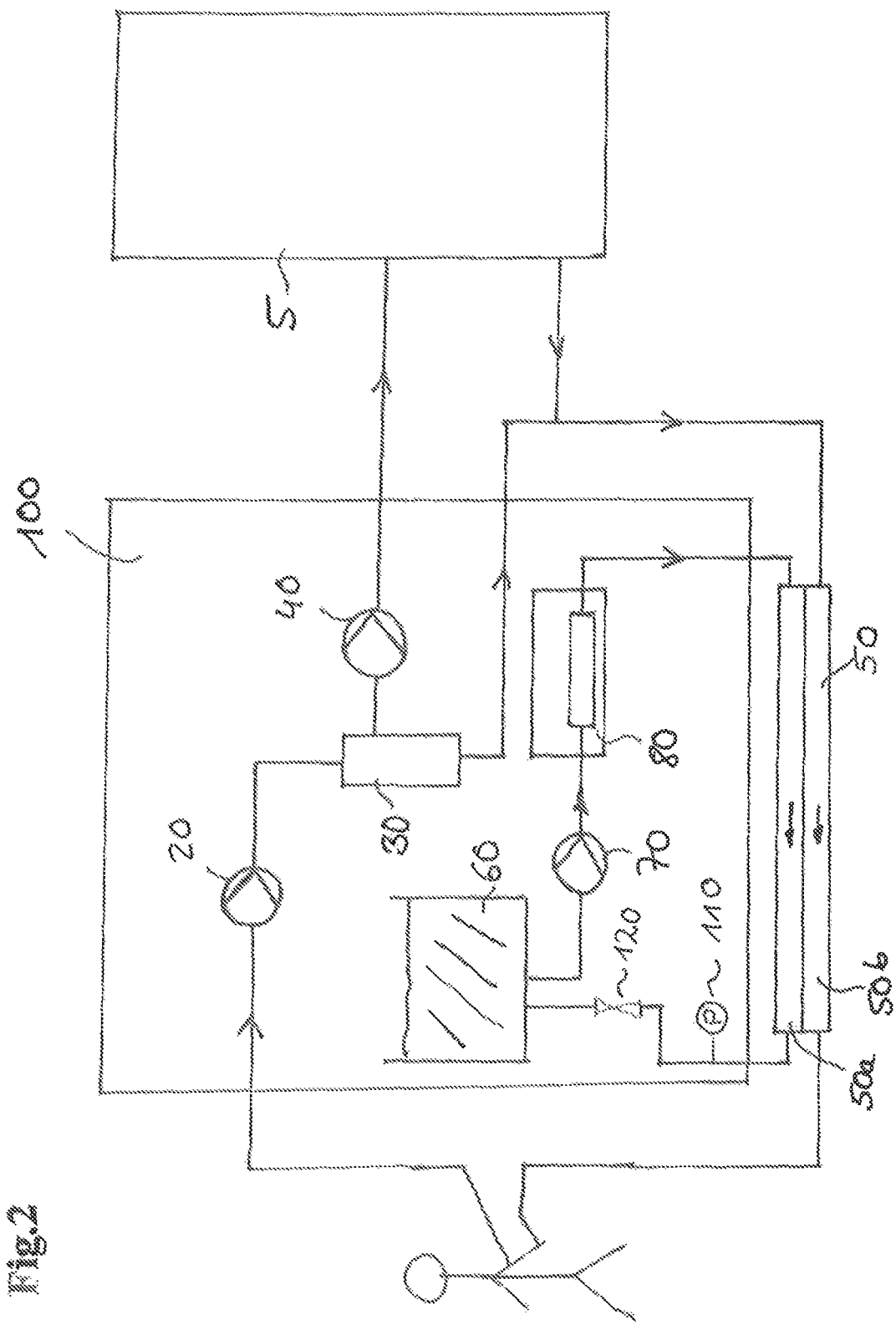

Further details and advantages of the invention will be explained in more detail with reference to a plurality of embodiments described in the following. The Figures show:

FIG. 1: a conventional therapeutic system for plasma purification using a known acute dialysis machine; and FIG. 2: a system representation with the blood treatment device in accordance with the invention for plasma purification.

The embodiment relates to a dialysis machine having an extracorporeal blood circuit which comprises one or more tubes which comprise(s) a multi-lumen tube in total or section-wise.

The tube has a single inner lumen which is flowed through by blood as well as a plurality of lumens which are arranged around it and surround the inner lumen. Six lumens of the second group can be provided overall, for example, which surround the central lumen.

The dialysis machine furthermore has at least one actuator by means of which the pressure in the outer lumens can be changed. At least one pressure sensor is furthermore provided which detects the pressure of the functional fluid.

Provision is made in this respect that at least two of the outwardly disposed lumens are connected to or communicate with one another such that the functional fluid flows, starting from the dialysis machine, through one of the second lumens, then undergoes a reversal of direction, and subsequently flows through another one of the second lumens back to the dialysis machine. The pressure sensor detects the pressure loss over this flow path or at least the pressure at the end of the second lumen through which the functional fluid flows back to the dialysis machine, If it is detected that the pressure loss is too large, a conclusion is drawn on the kinking of the multi-lumen tube.

The dialysis machine thereupon activates the actuator which increases the pressure in the outwardly disposed lumens, whereby the multi-lumen tube experiences a greater stability and the kink pint is effectively removed.

The functional fluid, which can be air or water, for example, can also take over other tasks such as the transfer of information between the patient and the dialysis machine or the transfer of energy, for example for actuating a valve, etc.

An alternative application case of the multi-lumen tube set in accordance with the invention is shown in FIG. 2. The illustration shows a system setup with an acute dialysis machine 100 that is used for plasma purification.

As in the representation of FIG. 1, the blood is conveyed from the patient through the blood pump 20 to the dialyzer 30. The plasma filtered there by means of the filtrate pump 40 enters into the device 5 for purification from where it is fed back into the blood line returning to the patient after the purification. Unlike in the prior art, however, no external heating device is required; a multi-lumen tubing set 50 is used instead. The purified blood to be returned to the patient flows in one lumen 50b of the tubing set 50; the other lumen 50a transports a heated saline solution to heat the blood in the lumen 50b to a specific temperature.

The saline solution originates from an internal reservoir 60 of the dialysis machine 100 and is brought to the desired temperature level by means of a pump (actuator) 70 present in the acute dialysis machine and previously unused and by means of a heating element 80. The pump 70 and the heating element 80 typically serve the heating of the substituate or of a dialysis solution in standard acute dialysis processes. The use of this apparatus 60, 70 contrary to its purpose for a heating fluid that heats the patient blood to be returned by means of the tubing set 50, through pressure sensor 110 and valve 120, makes an external heating device superfluous in therapeutic processes using plasma replacement. The heating fluid moves from the tubing set 50 back to the reservoir 60 again.

In the representation, blood and heating fluid flow through the lumens 50a, 50b in the same direction; however a counter-flow process is likewise conceivable. More than one lumen can furthermore also be provided for the flowing through of the tube piece 50 with heating fluid.

The invention claimed is:

1. A device useful in blood treatment comprising
an extracorporeal circuit formed at least sectionally by a multi-lumen tube having a second lumen arranged about a first lumen, wherein the second lumen is one lumen or a group of lumens and the first lumen is one lumen or group of lumens, wherein the first lumen is arranged in the circuit to transport a blood fluid, and wherein the second lumen is arranged in the circuit to transport a functional fluid to and from the device for affecting the blood fluid in the first lumen,
at least one pressure sensor arranged at the end of the second lumen transporting functional fluid back to the dialysis machine and configured to determine a pressure loss of the at least one functional fluid when in the second lumen, and
an actuator in communication with the second lumen and the at least one pressure sensor, wherein the actuator is configured to increase the pressure of the functional fluid when in the second lumen, when a loss in the pressure of the functional fluid is determined by the at least one pressure sensor indicative of a kinking of the multi-lumen tube by the second lumen, in such a way that the kinking of the multi-lumen tube by the second lumen is remedied.

2. A device in accordance with claim 1, characterized in that the functional fluid is a gas or a liquid.

3. A method of operating a device in accordance with claim 1, with the method comprising changing the pressure of the functional fluid in the second lumen by increasing pressure in the second lumen when a kinking of the multi-lumen tube is detected.

4. A method in accordance with claim 3, characterized in that the kinking of the tube is detected in that the functional fluid is conducted through at least one lumen of the second lumen and a pressure drop of the functional fluid is measured on the throughflow, with provision being made that at least two lumens of the second lumen are connected to one another, with the functional fluid flowing through a lumen of the at least two lumens in a first direction and subsequently through a further lumen of the at least two lumens in a second direction opposite to the first direction and with the pressure drop of the functional fluid being measured on the throughflow of the lumen and the further lumen of the at least two lumens.

5. A method in accordance with claim 3, characterized in that the pressure of the functional fluid in the second lumen is increased for so long until the measured pressure drop falls below a specific limit value.

6. A method in accordance with claim 3, characterized in that the method comprises the step of transferring information and/or energy by a pressure change or by pressure pulses of the functional fluid.

7. A method in accordance with claim 6, characterized in that at least one valve is provided which is arranged such that it is actuated by the pressure change of the functional fluid.

8. A method in accordance with claim 3, characterized in that the method comprises the steps of measuring the pressure of the fluid flowing through the first lumen and changing the pressure of the functional fluid in dependence thereon.

9. A dialysis machine comprising a device in accordance with claim 1, wherein the second lumen is filled with the functional fluid.

10. A method of operating the device in accordance with claim 2, with the method comprising heating a blood return line to a patient during dialysis treatment of the patient, wherein the blood return line comprises the first lumen, and wherein a heating fluid flows through the second lumen to heat blood returning to the patient in the first lumen to a required temperature.

11. A dialysis machine in accordance with claim 9 having a patient blood return line, wherein the return line comprises the first lumen, such that, when heating fluid flows through the second lumen, blood returning to the patient through the first lumen is heated.

12. A dialysis machine in accordance with claim 11 wherein the second lumen is connected to an internal heating fluid reservoir, the second lumen is connectable to a heating fluid reservoir and an internal pump for conveying the fluid to the second lumen, or the second lumen is connected to an internal heating element for temperature control of the heating fluid.

13. A dialysis machine in accordance with claim 12, characterized in that the internal pump is a non-used dialysate pump or substitute pump, and the internal heating element is a non-used heating element or a substitute heating element.

14. A blood treatment machine for therapeutic apheresis comprising the device according to claim 1 and having a patient blood return line, wherein the return line comprises the first lumen, such that, when heating fluid flows through the second lumen, blood returning to the patient through the first lumen is heated, in particular for therapeutic apheresis.

* * * * *